(12) United States Patent
Robinson

(10) Patent No.: US 6,936,269 B2
(45) Date of Patent: Aug. 30, 2005

(54) INSECT REPELLENT SUBSTRATE FOR HEADWEAR

(75) Inventor: Veronica S. Robinson, Maddington (AU)

(73) Assignee: Licebusters International R&D Pty Ltd., Nedlands (AU)

(*) Notice: Subject to any disclaimer, the term of this patent is extended or adjusted under 35 U.S.C. 154(b) by 0 days.

(21) Appl. No.: 09/341,299

(22) PCT Filed: Jan. 9, 1998

(86) PCT No.: PCT/AU98/00010
§ 371 (c)(1),
(2), (4) Date: Aug. 31, 1999

(87) PCT Pub. No.: WO98/30124
PCT Pub. Date: Jul. 16, 1998

(65) Prior Publication Data
US 2003/0150467 A1 Aug. 14, 2003

(30) Foreign Application Priority Data
Jan. 9, 1997 (AU) .............................................. P 4502
Apr. 17, 1997 (AU) .............................................. P 6268

(51) Int. Cl.$^7$ ........................ A01N 25/10; A01N 25/32; A01N 65/00

(52) U.S. Cl. ................ 424/409; 2/4; 119/856; 424/403; 424/405; 424/406; 424/407; 424/411; 424/420; 424/736; 424/742; 424/761; 428/484; 514/65; 514/74; 514/531

(58) Field of Search ................ 424/403, 405–407, 424/409, 411, 420, 77, 736, 742, 761; 119/653–656, 660, 856–858, 860; 428/484; 2/4; 514/65, 74, 53

(56) References Cited

U.S. PATENT DOCUMENTS

| | | | |
|---|---|---|---|
| 246,335 A | * 8/1881 | Page | 424/403 |
| 2,535,089 A | * 12/1950 | Newhan et al. | 424/403 |
| 2,537,023 A | * 1/1951 | Barrett et al. | 424/403 |
| 2,555,330 A | * 5/1951 | Gates | 424/403 |
| 3,767,785 A | * 10/1973 | Bordenca | 424/29 |
| 4,164,561 A | * 8/1979 | Hautmann | 424/29 |
| 4,671,960 A | * 6/1987 | Thielen et al. | 424/195.1 |
| 4,862,832 A | * 9/1989 | Metzner et al. | 119/86 |
| 5,003,635 A | * 4/1991 | Peterson | 2/69 |
| 5,208,029 A | * 5/1993 | Plummer et al. | 424/405 |
| 5,698,209 A | * 12/1997 | Shono et al. | 424/405 |
| 6,015,570 A | * 1/2000 | Tucci et al. | 424/403 |

FOREIGN PATENT DOCUMENTS

JP          63307801     *  2/1988

OTHER PUBLICATIONS

Lesser: Drug & Cosmetic Industry p. 150 48/2, Feb. 1941.*
Cassida: Pyrethrum p. 235–237, 136, 137, 1973.*

* cited by examiner

Primary Examiner—Neil S. Levy
(74) Attorney, Agent, or Firm—Stites & Harbison PLLC; B. Aaron Schulman

(57) ABSTRACT

An insect repellent substrate (10) includes a fabric base material (12) made of felt which is impregnated with a repellent carrier composition (14). The carrier composition (14) includes a mixture of wax and a naturally occurring insect repellent such as pyrethrum oil. The carrier composition (14) may also include scented or aromatic oils such as citronella oil, rosemary oil, eucalyptus oil and neem oil. Strips of the fabric base material may be attached to headwear such as a headband or cap so that it is in contact with the wearer's hair or body. Active constituents of the carrier composition (14) provide effective treatment and prevention of headlice and other parasitic insects.

30 Claims, 2 Drawing Sheets

INSECT REPELLENT SUBSTRATE FOR HEADWEAR

FIELD OF THE INVENTION

The present invention relates to an insect repellent substrate for repelling lice and the like insects, and relates particularly, though not exclusively, to headwear having a strip of said insect repellent substrate provided in connection therewith.

BACKGROUND TO THE INVENTION

Infestations of headlice and other parasitic insects are a perennial problem, particularly in schools where the lice are easily transmitted from child to child. Up to the present time there has been very little that one can do to prevent a child from being infected with headlice. Regular inspection to identify nits, which are the eggs of lice, is the only way to detect an infestation. Treatment includes combing the hair with a fine-toothed comb and/or washing the hair with a special shampoo which contains chemical substances designed to kill the lice and nits.

However, the shampoos that are currently available to treat headlice typically contain harsh synthetic chemicals such as permethrium, piperonyl butoxide and organophosphates which have been known to cause skin irritation. In the United Kingdom across the counter sales of shampoos containing organophosphates have recently been banned because of health concerns.

A further disadvantage with shampoos is that they only treat the hair at the time of use. They do not prevent the child from being re-infected when he/she returns to school.

SUMMARY OF THE INVENTION

The present invention was developed with a view to providing a lice repellent substrate suitable for headwear that can kill any lice present in the hair as well as preventing any further infestation of headlice. Although the present invention will be described primarily in relation to the treatment and prevention of lice infestation, it is to be understand that it also has application to the treatment and/or prevention of infestations of other parasitic insects such as fleas. Furthermore, although the insect repellent substrate is particularly suitable for headwear it may also have other applications such as, for example, under a pillow at night.

According to one aspect of the present invention there is provided an insect repellent substrate for repelling lice and the like insects and for attachment to a garment, the substrate comprising:

a strip of fabric base material impregnated with a repellent carrier composition and being adapted to attach to the garment in a manner that will ensure continuous contact of the insect repellent substrate with the wearer's hair or body, the carrier composition including a mixture of wax and an insect repellent whereby, in use, the wearer's body heat causes the carrier composition to soften to provide a controlled release of the insect repellent from the fabric base material.

Preferably the insect repellent is a naturally occurring compound. More preferably the insect repellent includes an extract from the pyrethrum flower. Most preferably the insect repellent is pyrethrum oil. Advantageously the carrier composition further includes one or more scented or aromatic oils. More preferably the carrier composition includes citronella oil and rosemary oil, which are also mild insect repellents. Preferably the carrier composition further includes neem oil, a naturally occurring insect repellent.

Typically the wax is a paraffin wax. Alternatively, the wax is beeswax obtained from honeycomb of the bee.

Preferably the carrier composition includes between 0.5% to 6.0% by volume of pyrethrum. Preferably the carrier composition includes between 0.5% to 4.0% citronella oil. Preferably the carrier composition includes between 0.5% to 5.0% rosemary oil. Preferably the carrier composition includes between 3.0% to 9.0% neem oil. Preferably the carrier composition also includes between 0.5% to 6.0% eucalyptus oil.

Most preferably the carrier composition includes 30 mls of pyrethrum (50% w/w), 20 mls of citronella, 25 mls of rosemary and 45 mls of neem oil to every one litre of wax. Preferably the fabric base material is a felt material; most preferably a polyester/cotton blend felt material.

According to another aspect of the present invention there is provided a method of manufacturing an insect repellent substrate for repelling lice and the like insects for attachment to a garment, the method comprising the steps of:

producing a repellent carrier composition by:
  heating a wax to a liquid state; and,
  mixing an insect repellent with the liquid wax;
dipping a strip of fabric base material into the carrier composition whilst still in the liquid state for a sufficient length of time to allow the base material to absorb some of the carrier composition;
allowing the impregnated strip of base material to cool so that the carrier composition solidifies on the base material to form said insect repellent substrate; and,
attaching the substrate to the garment whereby, in use, the wearer's body heat causes the carrier composition to soften to provide a controlled release of the insect repellent from the fabric base material.

Preferably the insect repellent is a naturally occurring compound. More preferably the insect repellent includes an extract of the pyrethrum flower. Most preferably the insect repellent includes pyrethrum oil.

Preferably the step of producing the repellent carrier composition further includes mixing one or more scented or aromatic oils with the liquid wax. Most preferably the scented oils include citronella oil and rosemary oil, which are also mild insect repellents.

Preferably the step of producing the carrier composition further includes mixing neem oil with the liquid wax.

Typically the garment is an item of headwear such as, for example, a headband, hat or a cap. Alternatively the garment is an animal garment, such as, for example, a flea collar or a coat.

BRIEF DESCRIPTION OF THE DRAWINGS

In order to facilitate a better understanding of the nature of the invention a preferred embodiment of the insect repellent substrate will now be described in detail, by way of example only, with reference to the accompanying drawings, in which.

DETAILED DESCRIPTION OF THE PREFERRED EMBODIMENT

Figure 1:
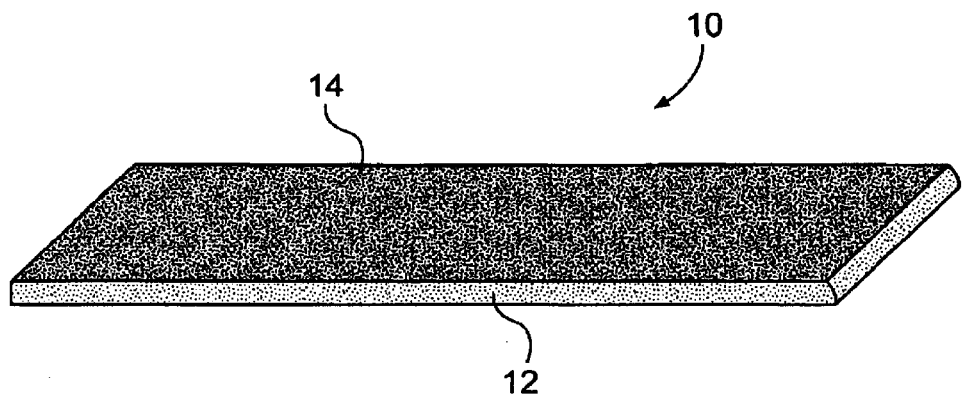
FIG. 1 illustrates a typical piece of insect repellent substrate in accordance with the invention.

A preferred embodiment of the insect repellent substrate 10 as shown in FIG. 1 comprises a piece of fabric base material 12 impregnated with a repellent carrier composition 14. Any suitable fabric base material may be employed. In the preferred embodiment the fabric base material is a felt material. A felt material made from a cotton and polyester blend was found to be most suitable. The fabric base material 12 should preferably be sufficiently absorbent to absorb the carrier composition 14 in a liquid state whilst retaining a degree of flexibility when impregnated with the carrier composition 14 in its solid state.

The repellent carrier composition 14 includes a mixture of wax and an insect repellent. In this embodiment the wax is a paraffin wax, although a naturally occurring wax such as beeswax obtained from honeycomb of the bee may also be used. The wax typically has a melting point of between 60° C. to 65° C. The insect repellent employed in the carrier composition is preferably a naturally occurring compound. In the preferred embodiment the insect repellent includes an extract from the pyrethrum flower. Pyrethrins, the active constituent of pyrethrum flowers, are commonly used as a contact insecticide in fly-sprays. Pyrethrins are noted for the very rapid paralysis (knock-down) effect produced on flies, mosquitoes and other insects. Chemically modified pyrethrins, such as permethrium, have greater persistence and other commercially desirable properties. In the present invention, it is preferred to use the naturally occurring pyrethrum pale extract from pyrethrum flowers grown in Kenya. Typically, a diluted pyrethrum solution (50% w/w PBK) in an odourless isoparaffin solvent is used. Typically between 0.5% to 6.0% by volume of the pyrethrum oil solution is employed in the repellent carrier composition.

Advantageously the carrier composition 14 also includes one or more scented or aromatic oils. The addition of scented or aromatic oils is desirable in order to give the repellent carrier composition a pleasant aroma or scent. In addition, selected naturally occurring scented oils, such as citronella oil, rosemary oil and eucalyptus oil act as mild insect repellents and/or have other medicinal qualities. Thus, for example, rosemary oil is a mild insect repellent and is also thought to help to relieve headaches. Citronella oil also acts as an insect repellent and provides a fresh citrus aroma. It also helps to dry up congestion of the nasal passages. Eucalyptus oil is an antiseptic and eucalyptus vapours act to relieve congestion and breathing difficulties through the nasal passages.

The carrier composition preferably also includes neem oil extracted from the neem tree, which is a long-lasting insect repellent. Through extensive experimentation the inventor has found that the repellent carrier composition should preferably include a mixture of between 0.5% to 4.0% by volume citronella oil, 0.5% to 5.0% by volume rosemary oil and 3.0% to 9.0% neem oil together with 0.5% to 6.0% by volume of pyrethrum. These proportions were found to give the carrier composition sufficient active components to kill any lice or nits present, balanced with the repellent and aromatic properties of the constituents. A carrier composition which includes 30 mls of pyrethrum (50% w/w), 20 mls of citronella, 25 mls of rosemary and 45 mls of neem oil to every one litre of wax has been found to be particularly effective.

Figure 2:
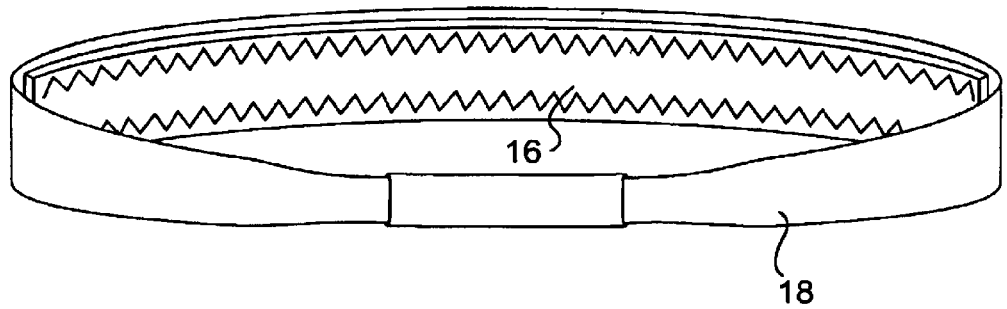
FIG. 2 illustrates a headband having a strip of the insect repellent substrate of FIG. 1 attached thereto.

The wax in the carrier composition 14 provides a controlled release of the insect repellent from the fabric base material 12. In use, the base material 12 may be sewn on the inside of a garment in a manner that will ensure contact with the wearer's hair or body. For example, a strip 16 of the insect repellent substrate may be sewn to the inside of a headband 18 as shown in FIG. 2. Strips of the impregnated felt material are cut to various sizes, ranging from 20 cm to 24 cm in length and from 2.5 cm to 5.0 cm in width, are sewn into stretchy cotton fabric to form the headband. Alternatively, strips of the impregnated felt may be sewn onto or adhered to an existing headband. When the headband 18 is worn on the wearer's head the strip 16 of insect repellent substrate will be in contact with the wearer's hair. The body temperature of the wearer will cause the wax in the substrate to soften allowing the active and aromatic constituents of the repellent carrier composition to be slowly released onto the wearer's hair and scalp. The controlled and continuous release of active constituents onto the wearer's hair and scalp not only kills any existing headlice and/or nits but also prevents any further infestation. In use, the strip 16 of insect repellent substrate has been found to provide effective treatment and prevention of headlice for approximately 6 to 8 weeks. After this length of time most of the active constituents of the repellent carrier composition are found to have leached out or evaporated from the fabric base material.

The insect repellent substrate 10 is relatively simple and inexpensive to manufacture. Typically, strips of the felt material are cut to size and dipped in a preheated (to approximately 70° C.) wax solution containing the pyrethrum, citronella, rosemary and neem oil in the proportions noted above. The pyrethrum oil, citronella oil, rosemary oil and neem oil are simply added to the melted wax and readily mix with the wax in view of their oily composition. The felt strips absorb the wax solution after two or three minutes and then the impregnated felt strips are allowed to cool so that the wax solution solidifies on the felt fabric. After approximately two minutes of cooling the impregnated felt strips are ready to be attached to any suitable garment. The strips of insect repellent substrate may be attached to the garment using any appropriate fastening, for example, by sewing, an adhesive or using a hook and loop fastener system such as Velcro (registered trade mark).

Figure 3:
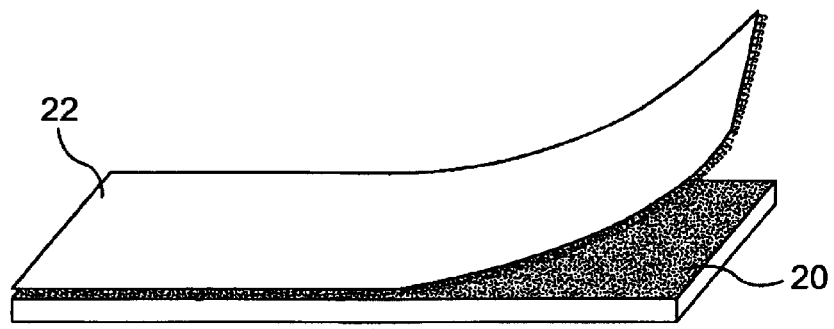
FIG. 3 illustrates a strip of insect repellent substrate in accordance with the invention having a strip of hook and loop fastener material fixed thereto; and, FIG. 4 illustrates a baseball cap having several strips of the insect repellent substrate illustrated in FIG. 3 attached thereto.
Figure 4:
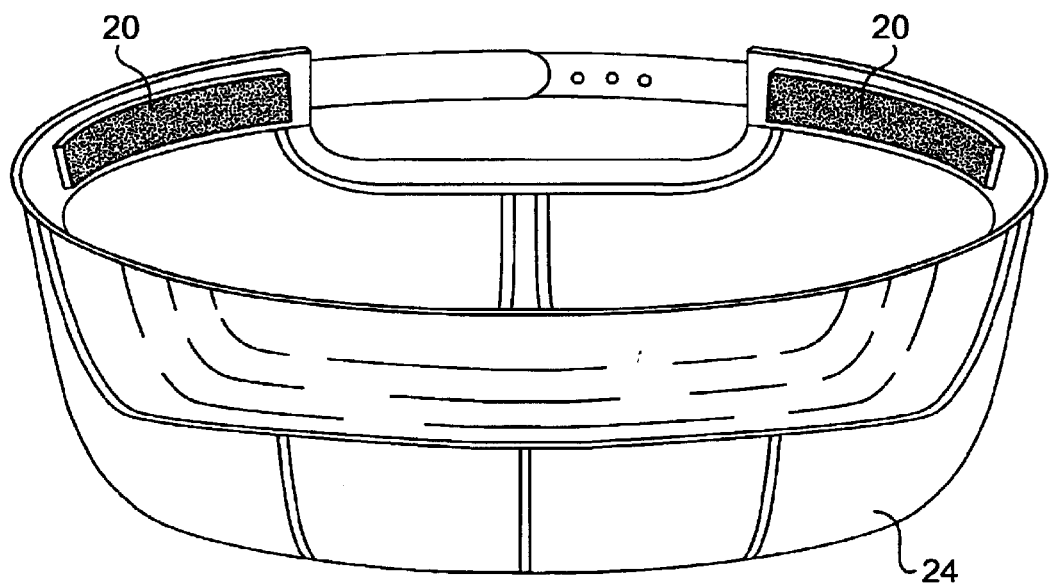

FIG. 3 illustrates a strip 20 of the insect repellent substrate having a strip of hook and loop fastener material 22 fixed thereto. One part of the hook and loop fastener is glued to the felt base material 10 and the other part can be attached to a garment by sewing or using a suitable self-adhesive. A baseball cap 24 is illustrated in FIG. 4 (shown upside down) having several strips 20 of the insect repellent substrate attached to an inside surface of the cap where they will be in direct contact with the hair and/or scalp of the wearer. Similar strips of the insect repellent substrate can be attached to suitable animal garments, such as a flea collar worn by pet dogs and cats or on the bridle or protective coat worn by horses, sheep and other livestock. In this connection, the repellent properties of the active constituents of the repellent carrier composition have also been found to repel flies and mosquitoes.

A piece of the insect repellent substrate 10 may also be used as a "night breather" to reduce congestion and aid breathing during sleep. A carrier composition containing 30 mls by volume of citronella, 20 mls by volume of rosemary, 30 mls by volume of eucalyptus and 5 mls by volume of pyrethrum to every litre of wax, has been found particularly effective as a night breather. A piece of the insect repellent substrate approximately 20 cm×14 cm is placed in the pillowcase or under the bottom sheet next to the mattress at the head of the bed. The night breather has also been found to relieve snoring in many cases. In this application, the insect repellent substrate 10 may also act to treat and prevent bed infestations of lice, fleas and dust mite.

Now that a preferred embodiment of the insect repellent substrate has been described in detail, it will be apparent that it has several advantages over the prior art methods of treating headlice, including but not limited to the following advantages:

(a) it provides immediate treatment as well as long-lasting prevention;

(b) the naturally occurring repellents employed are less hypo-allergenic and more environmentally friendly than the prior art synthetic compounds;

(c) the scented or aromatic oils produces a fresh herbal aroma;

(d) it is relatively simple and inexpensive to manufacture; and, (e) it is inconspicuous and can be easily attached to commonly worn headwear by children, who are particularly self-conscious about such things.

Numerous variations and modifications to the described embodiment will suggest themselves to persons skilled in the art, in addition to those already described, without departing from the basic inventive concepts. For example, other types of suitable fabric base material may be employed. All such variations and modifications are to be considered within the scope of the present invention, the nature of which is to be determined from the foregoing description and the appended claims.

The claims defining the present invention are as follows:

1. An insect repellent insert for repelling lice and other parasitic insects and for attachment to the inside of a garment to be worn by a person, the insert comprising:

an insert strip of an absorbent fabric base material impregnated with a repellent carrier composition, the carrier composition being solid at a temperature below body temperature, the insert strip being adapted to attach to the inside of a garment in a manner that will ensure continuous contact of the portion of the garment containing the insect repellent substrate with the wearer's hair or body, the carrier composition including a mixture of wax and an insect repellent in proportions such that when exposed to body temperature heat, the insect repellent will be controllably released from the carrier composition, the insect repellent being present in an amount that is non-toxic to a person but sufficient to treat and prevent infestations of lice and other parasitic insects on a person whereby, in use, when the garment is worn by a person such that the portion of the garment containing the insect repellent substrate is in contact with hair or skin of the person, and the person's body heat causes the insect repellent to be controllably released from the absorbent fabric base material to the hair or skin of the person so as to treat or prevent infestations of lice and other parasitic insects.

2. An insect repellent insert as defined in claim 1, wherein the insect repellent is a naturally occurring compound.

3. An insect repellent insert as defined in claim 2, wherein the insect repellent includes an extract from the pyrethrum flower.

4. An insect repellent insert as defined in claim 3, wherein the insect repellent is a pyrethrum solution.

5. An insect repellent insert as defined in claim 1, wherein the carrier composition further includes one or more scented or aromatic oils.

6. An insect repellent insert as defined in claim 5, wherein the carrier composition includes citronella oil and rosemary oil.

7. An insect repellent insert as defined in claim 2, wherein the carrier composition further includes neem oil.

8. An insect repellent insert as defined in claim 1, wherein the wax is a paraffin wax.

9. An insect repellent insert as defined in claim 4, wherein the carrier composition includes between 0.5% to 6.0% by volume of pyrethrum.

10. An insect repellent insert as defined in claim 9, wherein the carrier composition includes between 0.5% to 4.0% citronella oil.

11. An insect repellent insert as defined in claim 10, wherein the carrier composition includes between 0.5% to 5.0% rosemary oil.

12. An insect repellent insert as defined in claim 11, wherein the carrier composition includes between 3.0% to 9.0% neem oil.

13. An insect repellent insert as defined in claim 12, wherein the carrier composition also includes between 0.5% to 6.0% eucalyptus oil.

14. An insect repellent insert as defined in claim 13, wherein the carrier composition includes 30 mls of pyrethrum (50% w/w), 20 mls of citronella, 25 mls of rosemary and 45 mls of neem oil to every one litre of wax.

15. An insect repellent insert as defined in claim 1, wherein the absorbent fabric base material is a felt material.

16. An insect repellent insert as defined in claim 15, wherein the absorbent fabric base material is a polyester/cotton blend felt material.

17. A method of manufacturing an insect repellent insert for repelling lice and other parasitic insects for attachment to a garment to be worn by a person, the method comprising:

producing a repellent carrier composition by
heating a wax to a liquid state, and mixing an insect repellent with the liquid wax to form a mixture;
the wax and insect repellent being in proportions such that the carrier composition is solid at temperatures below body temperature and will controllably release the insect repellent at a temperature corresponding to the body temperature of a person;

dipping a strip of absorbent fabric base material into the carrier composition while still in the liquid state for a sufficient length of time to allow the absorbent base material to absorb some of the carrier composition and such that the insect repellent is present in an amount that is non-toxic to the person but sufficient to treat and prevent infestations of lice and other parasitic insects on a person;

allowing the impregnated strip of base material to cool so that the carrier composition solidifies on the absorbent base material to form said insect repellent insert; and, attaching the insert to the inside of a garment in a manner that will ensure continuous contact of the portion of the garment containing the insect repellent insert with the hair or body of a wearer of the garment, whereby, in use, when the garment is worn by a person such that the wearer's body heat causes the carrier composition to controllably release the insect repellent from the absorbent fabric base material insert to the hair or skin of the person.

18. A method of manufacturing an insect repellent insert as defined in claim 17, wherein the insect repellent is a naturally occurring compound.

19. A method of manufacturing an insect repellent insert as defined in claim 18, wherein the insect repellent includes an extract of the pyrethrum flower.

20. A method of manufacturing an insect repellent insert as defined in claim 19, wherein the insect repellent includes a pyrethrum solution.

21. A method of manufacturing an insect repellent insert as defined in claim 17, wherein the step of producing the repellent carrier composition further includes mixing one or more scented or aromatic oils with the liquid wax.

22. A method of manufacturing an insect repellent insert as defined in claim 21, wherein the scented oils include citronella oil and rosemary oil.

23. A method of manufacturing an insect repellent insert as defined in claim 17, wherein the step of producing the carrier composition further includes mixing neem oil with the liquid wax.

24. An insect repellent insert as defined in claim 1, wherein the garment is an item of headwear.

25. An insect repellent insert as defined in claim 24, wherein the garment is a headband and said insect repellent insert is sewn onto the inside of a stretch fabric forming the headband.

26. An insect repellent insert as defined in claim 1, wherein the insect repellent insert is removably attached to the garment using hook and loop fastening material.

27. An insect repellent insert as defined in claim 26, wherein the garment is a baseball cap.

28. An insect repellant insert as defined in claim 1 wherein the mixture comprises at least 76% by volume of the wax.

29. A method of manufacturing an insect repellant insert as defined in claim 17 wherein the mixture comprises at least 76% by volume of the wax.

30. An insect repellent insert for repelling lice and other parasitic insects and for attachment to the inside of a garment to be worn by a person, the insert comprising:

an insert strip of absorbent fabric base material impregnated with a repellent carrier composition, the carrier composition being solid at a temperature below body temperature, the insert strip being adapted to attach to the inside of a garment in a manner that will ensure continuous contact of the portion of the garment containing the insect repellent substrate with the wearer's hair or body, the carrier composition including a mixture of wax and an insect repellent comprising an extract from the pyrethrum flower in proportions such that the carrier composition will controllably release the insect repellent at a temperature corresponding to the body temperature of a person, the insect repellent being present in an amount between 0.5% to 6.0% by volume of said carrier composition, said amount being non-toxic to a person but sufficient to treat and prevent infestations of lice and other parasitic insects on a person whereby, in use, when the garment is worn by a person such that the portion of the garment containing the insect repellent insert is in contact with hair or skin of the person, the person's body heat causes the controlled release of the insect repellent from the absorbent fabric base material to the hair or skin of the person.

\* \* \* \* \*